United States Patent [19]

Weiss et al.

[11] 4,274,289
[45] Jun. 23, 1981

[54] TRANSDUCER POSITIONING SYSTEM FOR ULTRASONIC TIRE TESTING APPARATUS

[75] Inventors: Arnold A. Weiss; David C. Christensen; Bruce H. Sikkema, all of Minneapolis, Minn.

[73] Assignee: AMF Incorporated, Santa Ana, Calif.

[21] Appl. No.: 70,688

[22] Filed: Aug. 29, 1979

[51] Int. Cl.³ ............................................. G01N 29/04
[52] U.S. Cl. ........................................ 73/618; 73/634
[58] Field of Search ................. 73/599, 600, 618, 622, 73/633, 634, 640, 641, 642

[56] References Cited

U.S. PATENT DOCUMENTS

| | | | |
|---|---|---|---|
| 2,378,237 | 6/1945 | Morris | 73/618 X |
| 3,336,794 | 8/1967 | Wysoczanski et al. | 73/618 X |
| 3,670,562 | 6/1972 | Muto et al. | 73/634 |
| 4,117,733 | 10/1978 | Gugel | 73/634 |

Primary Examiner—James J. Gill
Attorney, Agent, or Firm—Orrin M. Haugen; Thomas J. Nikolai

[57] ABSTRACT

An articulated arm having first and second pairs of parallel spaced apart pivotable linkages associated with a tire casing holding fixture for moving an array of ultrasonic transmitting transducers to and from a location exterior to the tire casing and a location between the two sidewalls of the tire casing with the faces of the transducers being a predetermined spaced distance from the interior surface of the tread bearing portion of the casing. Only a single piston/cylinder type actuator linked to the arm is required to achieve the desired movement and positioning of the transducer array.

7 Claims, 10 Drawing Figures

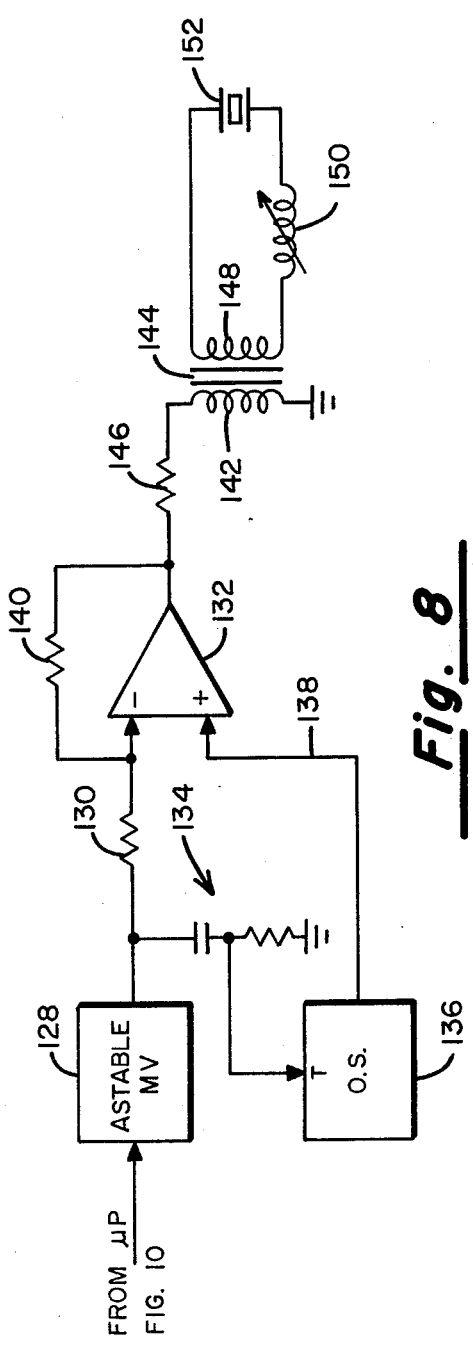
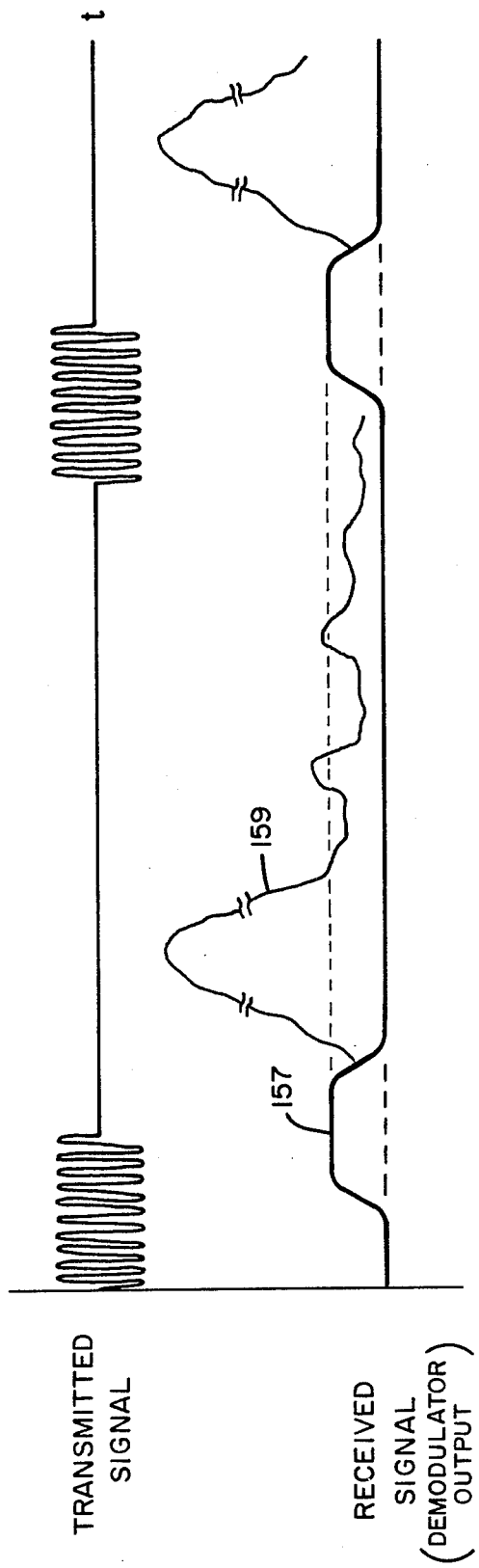
Fig. 8
Fig. 9

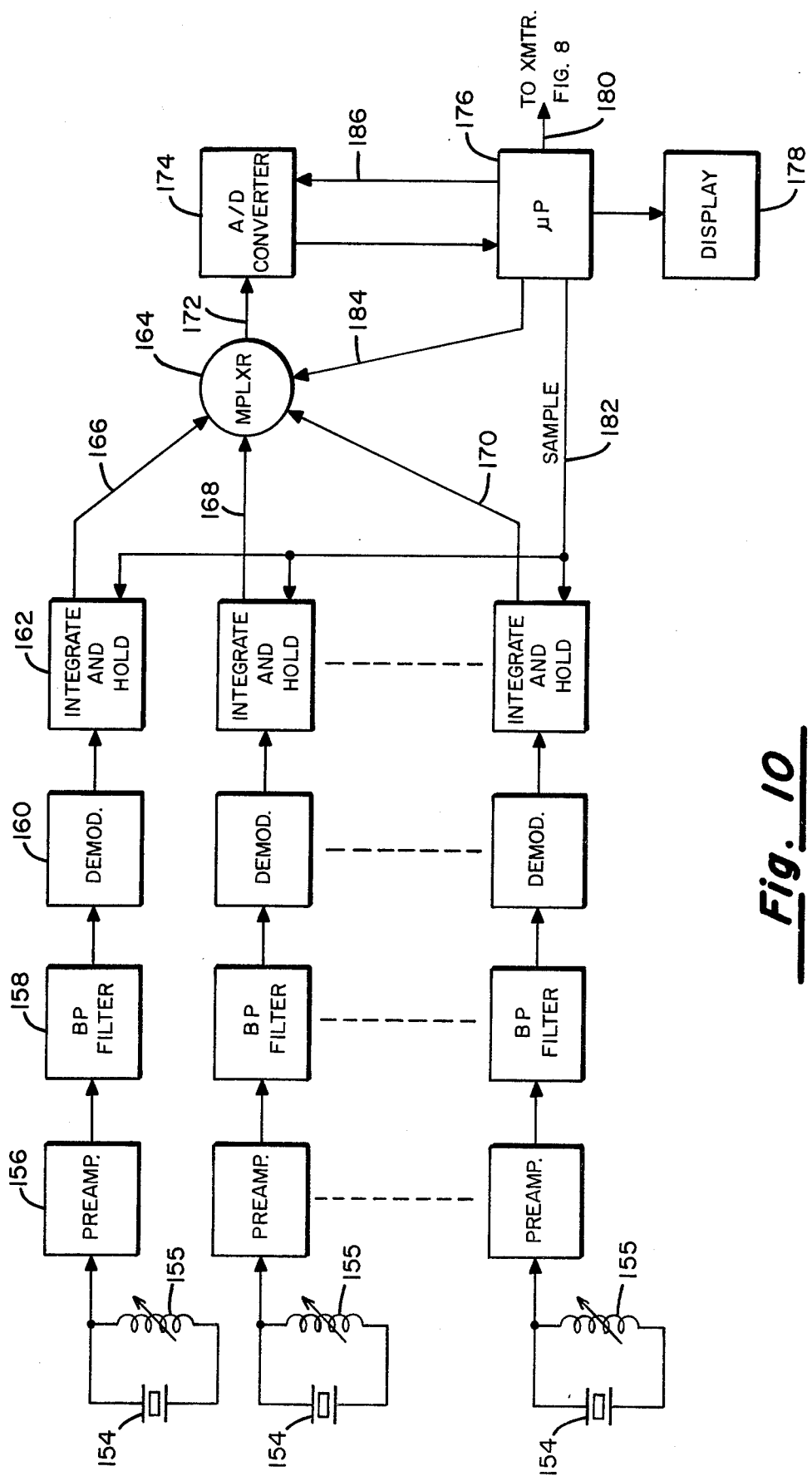

TRANSDUCER POSITIONING SYSTEM FOR ULTRASONIC TIRE TESTING APPARATUS

BACKGROUND OF THE INVENTION

I. Field of the Invention

This invention relates generally to apparatus for detecting flaws in tires and more specifically to an improved design of an ultrasonic transducer positioning device for use in such apparatus.

II. Discussion of the Prior Art

In the tire re-tread industry non-destructive, visual testing is performed on used tire carcasses to ensure that they are free from holes and separations. It is essential that the testing be accomplished in a minimum of time, yet with reliability standards maintained, whereby defective carcasses can be culled from those being selected for retreading.

Visual inspection is reasonably fast, however, separations and holes are missed due either to human error or to the lack of visible evidence of separations in high tread, radial or other casings.

For a number of years, now, machines have been developed to perform non-destructive tests on tires through the use of ultrasonic inspection techniques. For example, in the McCauley U.S. Pat. No. 3,882,717 there is disclosed an arrangement in which the tire to be inspected is placed in a liquid "coupling" medium and ultrasonic energy is transmitted thru the material under test and that energy passing through the tire is picked up by suitably oriented receiving transducers. By observing variations in the amplitude of the received signals, it can be determined whether voids have been scanned as the tire is rotated past the transmitting-/receiving transducers. This is the so-called "through transmission" method.

The apparatus and method of the McCauley Patent suffer from a number of drawbacks. First of all, the need for a liquid coupling medium makes the technique undesirable in that the subsequent handling of the wet tire tends to create a mess and is distasteful to the human operator. Furthermore, a subsequent drying step is required before further retreading steps can be accomplished. In addition, several revolutions of the tire are required in order to scan its entire surface. It is, of course, desirable to be able to cover the entire surface in a single revolution of the tire carcass under test, irrespective of its width and diameter, in order to reduce test time.

In the Halsey U.S. Pat. No. 4,059,989 there is described a method and apparatus for performing non-destructive flaw tests on vehicle tires wherein the need for a liquid ultrasound coupling medium is obviated. In this arrangement, thru-transmission is also used but the transmitting transducer and the receiving elements are placed in contact with the surface of the tire.

The rubbing contact between the transducers and the tire carcass creates a number of problems. First of all, the surface of the tire tends to be dirt laden and the scraping of the transducer across the tire surface usually causes dirt and dust to foul the transducer element resulting in the need for frequent and costly maintenance. Furthermore, rubbing surfaces create sonic energy and vibration which, when received by the receiving transducers may distort or otherwise affect the reliability of the test apparatus. The frictional engagement also leads to premature wear on the transducer. Foreign bodies, such as small stones or nails sticking through the tire may ruin the transducers.

The present invention obviates all of the above-mentioned drawbacks of prior art ultrasonic tire testing equipment. Specifically, the apparatus of the present invention does not require a liquid coupling medium, nor must the transmitting and/or receiving transducers be in direct contact with the tire carcass. Furthermore, the entire surface of most vehicle tires can be scanned in a single revolution of the tire, thus speeding up the overall rate at which a tire carcass may be fully inspected.

While dispensing with the need for a liquid coupling medium in the ultrasonic test unit is highly advantageous, the use of non-contact air coupling between the transmitting transducers, the object under test and the receiving transducers raise a number of ancillary problems. Specifically, to ensure that the entire tread surface of the tire casing is inspected during a single revolution of the tire casing about its central axis, it is necessary that plural ultrasonic transducers be arranged in an compact array such that the array can conveniently be inserted into and removed from the spacing between the side walls of the tire casing. Then too, the positioning of the transmitting array with respect to the tire under test is deemed to be somewhat critical in that unless proper spacing is maintained, standing wave patterns may be created which tend to render the overall system unduly sensitive to variations in geometry. Thus, it is rather essential that the transducer array be accurately positioned within the tire casing, yet automatically insertable and removable between the confines of the side walls.

SUMMARY OF THE INVENTION

The present invention provides an apparatus for accurately and precisely positioning an array of ultrasonic transducers with respect to a tire casing and which utilizes only a single hydraulically or pneumatically operated piston/cylinder device to effect the desired manipulation of the transducer array. In accordance with the present invention, there is provided an articulated arm comprised of first and second pairs of parallel, spaced apart, pivotally connected linkages. One end of the linkages comprising the first pair is pivotally connected to the framework of the fixture used to support and rotate the tire and the opposite ends of the linkages in this first pair are pivotally secured to a L-shaped member which, in turn, has the second pair of parallel linkages pivotally secured to it as well. The linkages comprising the second pair have their other ends secured to a transducer array support member and the piston rod of the actuator is connected to this same support member while the cylinder portion is pivotally secured with respect to the framework.

The linkages are dimensioned such that as the piston is retracted into the cylinder, the transducer array is first moved laterally toward the central opening of the tire and, upon reaching a position generally aligned with the center of the space defined by the tire's sidewalls, the lateral motion is arrested and followed by a movement of the transducer array toward the inside of the tread-bearing surface. This latter movement is also positively arrested when the transducers in the transmitting array are at a predetermined spaced relationship with respect to the inside of the tread-bearing surface.

The transducer array positioning mechanism of the present invention makes it possible to perform tire inspections using through transmission techniques in which the transmitter array and the associated ultrasonic transducer receiver array are both mounted in air and in a non-contacting relationship with the tire casing undergoing inspection. The present invention makes this type of testing possible in that it provides a rather simple, low-cost, yet highly accurate positioning mechanism, thus obviating several of the problems encountered in prior art ultrasonic tire inspection systems.

OBJECTS

It is accordingly a principal object of the present invention to provide an improved mechanism for moving and positioning a transducer array in an ultrasonic tire test system.

Another object of the invention is to provide a simplified arrangement of articulated linkage elements actuated by only a single piston/cylinder combination for precisely positioning a transducer array a predetermined distance from the inside tread surface of a vehicle tire.

Still another object of the invention is to provide a transducer array positioning mechanism for an ultrasonic tire inspection system which permits the array to first be moved in a lateral direction to a predetermined point generally aligned with the spacing between the parallel side walls of a tire casing and then followed by a axial translation of the array to a precise point between the sidewalls.

Yet still another object of the invention is to provide a transducer positioning assembly requiring only a single actuator, thereby eliminating the need for a programmer type control which would be required where plural actuators are employed.

These and other objects and advantages of the invention will become apparent to those skilled in the art from the following detailed description of a preferred embodiment when considered in conjunction with the accompanying drawings in which like numerals in the several views refer to corresponding parts.

DESCRIPTION OF THE DRAWINGS

FIG. 8 is a block diagram of the electrical circuit used to energize the transmitting transducers used in the system;

FIG. 9 are waveforms of the transmitted and received signals; and

FIG. 10 is a block diagram of the receiver electronics and associated computer control system.

DESCRIPTION OF THE PREFERRED EMBODIMENT

Figure 1:
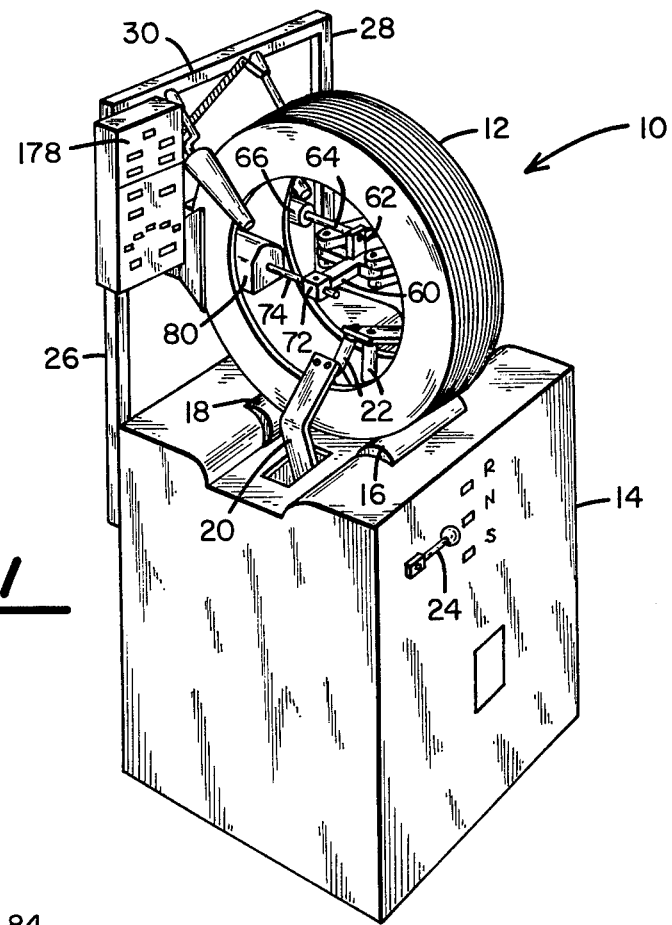
FIG. 1 is a perspective view of the tire testing apparatus of the present invention.

Referring first to FIG. 1, there is indicated generally by numeral 10 a device for non-destructively testing an object such as vehicle tire 12 for different types of flaws, specifically, holes and separations. The device includes a generally rectangular box-like base 14 containing motor driven drive rollers 16 and 18 on which the tire carcass 12 rests during the inspection process whereby the tire may be made to rotate about a central axis. The base 14 further includes air operated spreader arms 20 having rollers 22 journaled to the ends thereof. When actuated, the spreader arms descend into the interior of the casing and are retracted in such a fashion that opposed pulling forces are applied to the side walls of the tire, tending to expand or enlarge the opening in the neighborhood of the tire bead. The rollers 22 permit this force to be applied even while the tire casing itself is being rotated.

A control lever 24 is provided which may be disposed in any one of three positions namely "spread", "neutral", and "release". When in the release position, the spreader arms 20 are elevated relative to the generally horizontal base of the cabinet 14. When the lever 24 is moved to the "spread" position, air cylinders are operated, causing the spreader arms to move downward and outward so that the rollers 22 engage the inside surface of the side walls of the tire and apply a force tending to spread the side walls apart from one another. An electrical switch is provided which energizes a motor driving the rollers and causing the tire to rotate.

The structure thus far described, i.e., the cabinet base 14 with its drive rollers 16 and 18, its spreader arms 20 and its control lever 24 is commercially available from the Branick Division of Applied Power, Inc. of Fargo, North Dakota and, accordingly, it is unnecessary to describe in detail the internal construction of this device. The Branick manufactured device further includes a generally rectangular frame having vertical posts 26 and 28 affixed at their lower ends to the rear side surface of the cabinet 14 and a horizontal portion 30 extending between the vertical posts at the top ends thereof.

Figure 2:
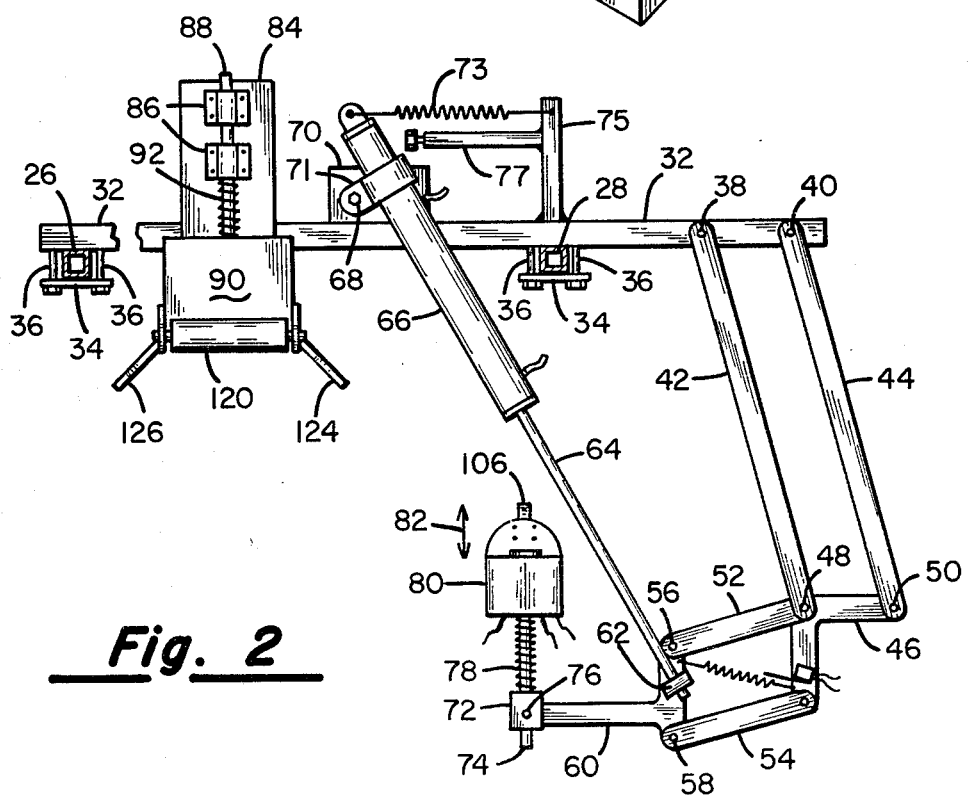
FIG. 2 is a top plan view of the receiver and the mechanism array used to position the transmitting transducer array within the tire casing.

Referring now to FIG. 2, a horizontally extending cross arm 32 is shown as being clamped to the vertically extending posts 26 and 28 by means of clamps, including clamp plates 34 and the clamping bolts 36, which pass through the plates 34 and the cross arm 32. Pivotally attached to the cross arm 32, as at 38 and 40, are a first pair of elongated linkages including linkages 42 and 44. Pivotally secured at the other ends of these last-mentioned linkages is a L-shaped connector member 46. The spacing between pivot points 38 and 40 corresponds to the spacing between the pivot points 48 and 50 on the connector member 46 so as to generally define a parallelogram configuration with the linkages 42 and 44. A second pair of linkages, including members 52 and 54, is also provided with the individual members being pivotally secured to the remaining leg of the L-shaped connector member 46. Pivotally attached to the opposite ends of the linkages 52 and 54 as at 56 and 58 is an actuator coupling member 60 to which is welded or otherwise affixed an upwardly extending stem 62 to which is affixed the end portion of a piston rod 64. The piston rod 64 extends into a pneumatic or hydraulic cylinder 66, which is pivotally connected as at 68 to a plate 70 by way of trunion 71. The plate 70 is, in turn, welded or otherwise affixed to the cross arm 32. The cylinder 66 extends beyond the trunion 71 and attached to the end portion thereof is a tension spring 73 whose other end is secured to a frame member 75 extending rearwardly from the cross arm 32. A stop member 77 attaches to the frame member 75 and is positioned so as to limit the clockwise rotation of the cylinder 66 about the pivoted trunion 71.

The end portion of the actuator coupling member 60 terminates in a generally rectangular block member 72 having an aperture passing therethrough. Fitted within this aperture is a cylindrical rod 74 which may be slotted so as to slidingly cooperate with a set screw 76 whereby rotation of the rod is inhibited. A compression-type spring 78 surrounds the rod 74 and abuts the block 72 and the rear surface of the transmitter transducer housing 80. Hence, this housing is normally urged away from the block 72 by the spring 78, but reciprocal movement of the housing in the direction of the double arrow 82 is allowed.

Approximately midway along the span of the cross arm 32 is located a plate-member 84 which is affixed to the cross arm 32 by any suitable fashion and on the upper surface thereof is a pair of slide blocks 86 which, too, are provided with a central bore or aperture for slidingly receiving a cylindrical rod 88. This rod may also be slotted so as to prevent rotation and only longitudinal translation. Affixed to the forward end of the rod 88 is the receiver transducer housing 90, the construction of which will be set out in greater detail hereinbelow. A spring 92 is disposed between the forward slide block 86 and the rear surface of the receiver housing and serves to normally urge the housing in a direction away from the slide blocks 86.

Figure 3:
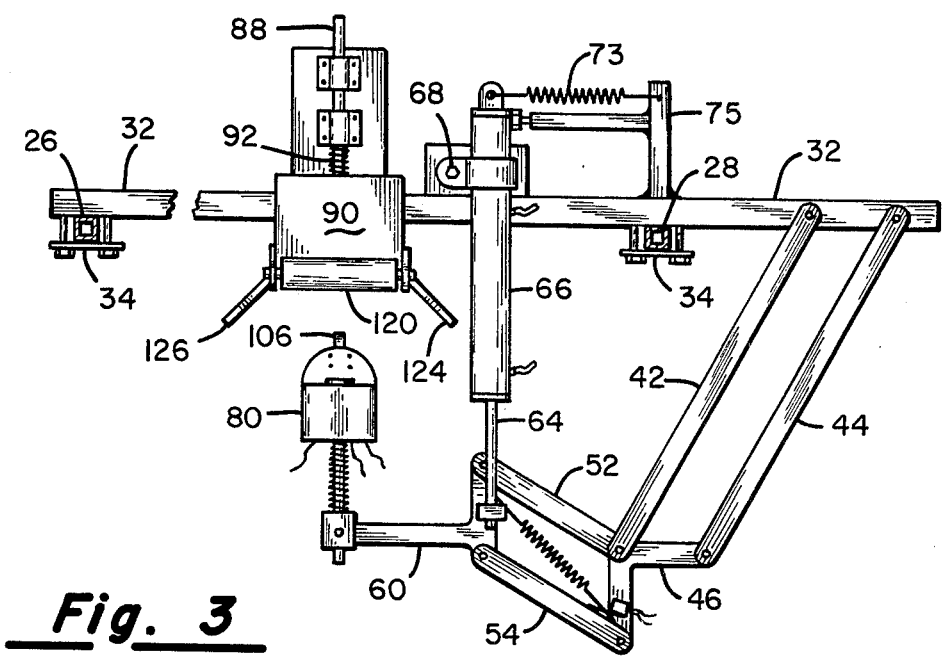
FIG. 3 is a further view of the apparatus of FIG. 2.

The partial view of FIG. 2 shows the orientation of the articulated actuator arms and the transmitting transducer housing prior to the time that a tire to be tested is installed on the drive rollers 16 and 18 of the base 14. When in this orientation, it can be seen that the piston rod 64 is fully extended outwardly from its associated cylinder 66. FIG. 3 illustrates the orientation of the several parts following actuation of the piston and cylinder whereby the piston rod 64 is withdrawn into the cylinder 66. The pneumatic control system may be coupled in with the controls associated with the spreader arms 20 such that when the control lever 24 is moved to its "spread" position, the actuation 66 will be operated. Because of the design of the articulated arm including the linkages 42-44 and 52-54, the path traversed by the transmitting transducer array housing 80 is first generally in a sideward direction but as the piston continues to be drawn into the cylinder, the housing 80 tends to move in a direction which is generally normal to the rear edge of the cabinet 14. As such, when a tire casing is disposed upon the drive rollers 16 and 18 as illustrated in FIG. 1 and the actuator mechanisms 64-66 is operated, the transducer array 80 will first be moved from a generally lateral position, into the zone in alignment with the space between the tire casing side walls and, subsequently, the housing 80 moves toward the casing wall in a generally straight line manner. Because the novel construction of the articulated piston actuated arm mechanism, the transducer housing 80 may be introduced into the space between the side walls of a tire casing without hitting or rubbing the side walls.

Initially, it can be seen that as the piston rod 64 is drawn into the cylinder 66 the spring 73 applies a force to the end of the cylinder 66, urging the cylinder to pivot about the pivoted trunion 71 journaled to the mounting plate 70 such that the transducing array 80 is moved laterally until the cylinder 66 strikes the adjustable stop member 77. The stop member is adjusted by the threaded screw in the end thereof so that the cylinder 66 will be generally aligned in a direction parallel to the side walls of the tire to be tested as the piston rod is drawn into its cylinder. The continued retraction of the piston rod 64 into the cylinder 66 then results in a movement of the transducer array 80 in the direction indicated by the double headed arrow 82, i.e., parallel to the side walls of the tire under test.

Figure 4:
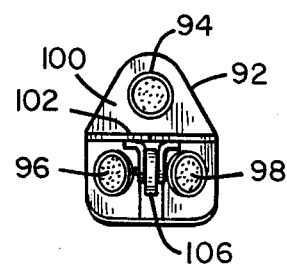
FIG. 4 is a front view of the transmitting transducer array used in the apparatus of FIG. 1.
Figure 5:
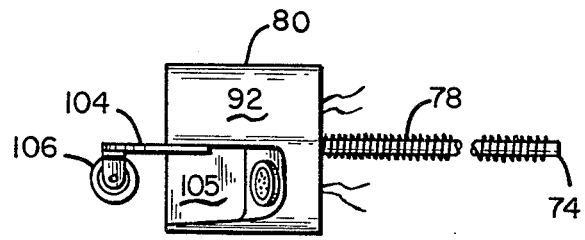
FIG. 5 is a side elevation of the transducing array of FIG. 4.

Referring now to FIGS. 4 and 5, the details of the construction of the transmitting transducer array and its associated housing will be described. The housing 80 includes a metal or plastic shroud 82 surrounding a plurality of piezoelectric or ferroelectric crystal ultrasonic transducers 94, 96 and 98 which are mounted in a faceplate 100. The transducers are preferably oriented so as to define the vertices of an isosceles triangle with the transducer at the apex arranged to generate a beam of ultrasonic energy which propages in a direction normal to the faceplate 100. The transducers 96 and 98 are, however, cocked at a predetermined angle with respect to the faceplate so as to project beams of ultrasonic energy at a divergent angle with respect to the direction of the beam produced by the transducer 94. In this fashion, it can be ensured that a transducer array of a sufficiently narrow width to fit between the side walls of a tire casing will be able to produce ultrasonic waves for "illuminating" the entire width of the tread area of a tire casing under test. For isolation purposes, the housing further includes a T-shaped baffle 102 with the cross portion of the T located between the upper transducer 94 and the two lower transducers 96 and 98. Similarly, the vertical leg of the T-shaped baffle 102 is disposed between the two lower transducers 96 and 98. Additional isolation is provided by the array geometry described above since the center transducer is disposed along the direction of travel thereby reducing the overlap between the three beams of ultrasonic waves.

Secured to the housing 92 and projecting outwardly from the front edge thereof is a roller mounting bracket 104 arranged so that a roller member 106 journaled thereto extends outwardly from the forward face of the transducer housing. The roller or wheel 106 is intended to run along the inside surface of a tire being tested and serves to maintain the transducers 94, 96 and 98 at an approximate desired spacing from the inner casing surface. This spacing is such that three transmitters can illuminate the total width of casings.

In practice, it has been found desirable to cover or otherwise coat the surfaces of the housing 92, the faceplate 100 and the baffle 102 with a suitable plastic foam material having good sound absorbing characteristics. This measure tends to reduce echoes and other sound reverberations while at the same time maintaining a desired directional orientation to the beams of ultrasonic energy exiting from the transducers 94, 96 and 98.

Figure 6:
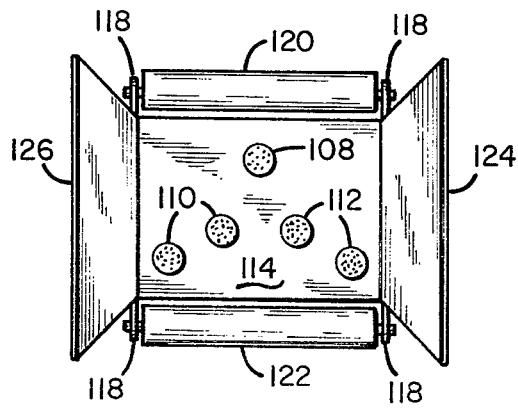
FIG. 6 is a front view of the receiver transducer array used in the apparatus of FIG. 1.
Figure 7:
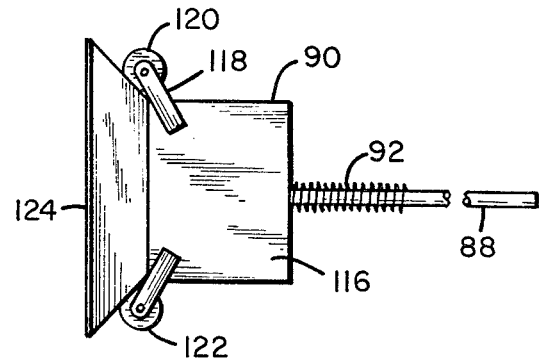
FIG. 7 is a side elevation of the receiving transducer array of FIG. 6.

With reference to FIGS. 6 and 7, the details of the construction of the receiver transducer array will next be set out. The piezoelectric ultrasonic transducers such as 108, 110 and 112 are disposed in a predetermined pattern and extend through apertures formed in a faceplate 114. The faceplate is surrounded by a box-like housing 116 (FIG. 7). The transducers 108, 110 and 112 are arranged so that their planar faces are generally parallel to the surface of the faceplate 114.

Affixed to the side walls of the housing 116 are a plurality of brackets 118 into which are journaled first and second horizontally extending parallel roller members 120 and 122, respectively. These rollers cooperate with the outside tread surface of the tire casing under test as the tire is rotated by the action of the drive rollers 16 and 18 (FIG. 1). Thus, the transducers 108, 110 and 112 are maintained in an approximate desired non-contact spacing with respect to the tire casing. The slotted rod 88 and the spring 92 provide a means for resiliently attaching the receiver housing 116 to the frame member so that out-of-round tire casings and/or tires of differing diameter can be accommodated.

Also affixed to the side walls of the housing 116 are first and second vertically extending baffle members 124 and 126. These baffle members may be fixedly secured to the housing and preferably extend at an obtuse angle with respect to the faceplate 114. The function of the baffle members 124 and 126 is to help reduce reverberations and, in this regard, it has been found expedient to affix a sound absorbing foam material to opposed sides of the baffle members as well as to the exterior surface of the faceplate 114.

Now that the details of the mechanical construction have been set out, consideration will be given to the electrical circuitry comprising the transmitter, receiver and signal processing devices employed.

Referring then to FIG. 8, there is shown a schematic diagram of the ultrasonic energy transmitter useful in the present system. An astable multivibrator 128 is adapted to be triggered by a control pulse from the system's digital computer in a fashion which will be set out more fully hereinbelow. The output from the astable multivibrator or oscillator 128 is coupled through a resistor 130 to the inverting input of an operational amplifier 132. The output from the oscillator 128 is also applied by way of a resistance-capacitance differentiating circuit to the trigger input terminal of a monostable multivibrator or one-shot circuit 136. The one-shot circuit 136 responds to the negative going spike of the differentiated output of the oscillator and the output from the one-shot circuit is applied by way of a conductor 138 to the non-inverting input of the operational amplifier 132. The amplifier 132 serves as a power amplifier, the gain of which is determined, in part, by the value of the feedback resistor 140 which is connected between the amplifier's output terminal and the inverting input terminal thereof and the input resistor 130.

The output from the power operational amplifier 132 is a burst of square wave signal having a zero D.C. component, of a frequency determined by the component values used in the astable multivibrator, and is applied to the primary winding 142 of a pulse transformer 144 by way of a resistor 146. The secondary winding 148 of the pulse transformer 144 is coupled in series with a variable tuning inductor 150 and the crystal 152 of the ultrasonic transmitting transducers. The tuning inductor permits a sharply defined burst of ultrasonic energy to be generated which is essential in limiting the effects of talk-around.

The astable multivibrator 128 is gated on and off by the output of a digital controller or computer, yet to be described, in such a fashion that the burst of square wave signals coming from the amplifier 132 is of a duration which is twice the transit time of the resulting sound waves from the face of the crystal driven transducer to the tire interface, namely 2 d/c where d is the transmitter to casing distance and c is the speed of sound in air. By doing so, problems which might otherwise be caused by standing wave patterns are reduced or eliminated. The repetition rate of the bursts is also controlled by the microprocessor or computer which is programmed to ensure that reverberations from a preceding burst have died out prior to the generation of the next succeeding burst. The resulting transmitted waveform, then, is that illustrated in the upper portion of FIG. 9.

The circuit of FIG. 8 may be used to drive all of the transducers in the transmitting array simultaneously, but it is desirable to utilize transducers of differing natural frequencies in the transmitting array to obtain signal separation and thereby minimize cross-talk between adjacent transmitting transducers. Thus for example one circuit can be used to drive the center transmitters, 94 at one frequency while a separate circuit drives the outside transmitters, 96 and 98, at a second frequency. In this way transmitter 94 does not interfere with 96 or 98. The outside transmitters can operate at one frequency since they are already separated by the transmitter array geometry.

The particular wave shape chosen i.e. a pulse modulated carrier having a zero D.C. component, offers the further advantage that it does not produce obnoxious, loud audible sound which would lead to operator dissatisfaction.

As is shown in FIG. 6, the receiving transducer array incorporates a plurality of ultrasound transducers 108, 110 and 112 for receiving the sound energy transmitted through the tire casing and for producing electrical signals proportional to the amplitude of the received energy. In order to obtain reasonable detectability of small flaws it has been found expedient to incorporate more receiving transducers so that the entire width of the tire may be considered as divided into individual channels, e.g., 5 channels with the receiver array as depicted in FIG. 6 of the drawings. When transducers of differing natural frequencies are used in the transmitting array the receiving transducers are matched thereto and also spacially disposed in a predetermined manner with the mating transmitting transducers.

Referring to FIG. 10, there is shown a block diagram of the electronic devices used in implementing the receiver module. The module itself is comprised of a plurality of channels, there being one channel for each of the receiver transducers employed in the receiver array. While only three such channels are shown in detail in FIG. 10, the vertical dashed lines are intended to represent additional receiver channels. In that all such channels are substantially identical, (except for the natural frequencies of the crystals employed), it is only necessary, for purposes of explanation, to describe one such channel in detail.

With this in mind, and with reference to FIG. 10, there is shown a receiving transducer 154 which may be any one of the ultrasonic transducers 108, 110 or 112 shown in FIG. 6. A variable inductor 155 is coupled in parallel with the transducer, allowing stagger tuning of the transducer to obtain a desired wide band characteristic, such that waves of short rise and fall times can be handled. The electrical output from this transducer is applied to a preamplifier stage 156 and the amplified output thereof is then applied to a bandpass filter 158 which preferably has a center frequency approximately equal to the frequency of the carrier developed by the transmitter electronics for that channel. Assuming crystals with a natural frequency of 23 KHz, the band width of the bandpass filter 158 may then be +/−3 KHz from said center frequency.

The output from the bandpass filter is applied to a demodulator or detector circuit 160 where the envelope of the received signal is reconstructed, the generally sinusoidal carrier signal being removed.

The output from the demodulator 160 is, in turn, applied to an integrate and hold circuit which functions to periodically sample the output from the demodulator network at time intervals determined by the system's microprocessor or computer and to perform an analog integration on this received signal.

Summarizing momentarily, every 30 milliseconds or so the system's computer typically sends a transmit pulse (FIG. 9) to the transmitter electronics of FIG. 8 to produce a pulse burst approximately ½ millisecond long and at about the crystal frequency. At the end of this period, the microprocessor type controller gates off the transmitter and a zero signal level is maintained until the next transmit pulse is initiated. As a result of this transmitted pulse, first ultrasonic energy signal propagates in the air from the transmitter transducers to the surface of the tire, through the tire, and then into the receiving transducer array. The "through" pulse is identified by numeral 157 in the lower waveform of FIG. 9. In addition to the received "through" pulse 157, a second or "talk-around" ultrasonic signal will also reach the receiving transducers. This "talk-around" signal is identified by numeral 159 in FIG. 9 and includes all ultrasonic energy reaching the receiving transducers by a path other than through the tire carcass. The electrical output from the individual transducers comprising the receiving array are fed to individual receiving channels, each consisting of a preamplifier followed by a bandpass active filter, followed by a full wave rectifier for demodulation, followed by an integrate and hold circuit. The computer gates the integrate and hold circuit in a way to accomplish integration of the signal during a time period which starts at the arrival of the "thru" pulse and stops before the arrival of the "talk-around" pulses. In this case the gating interval is ½ millisecond corresponding to the transmitter burst time since system geometry assures that this is sufficient to block "talk-around".

Continuing then, each receiver channel has its integrate and hold circuit 162 connected as an individual input to an analog multiplexer circuit 164. This circuit operates in a conventional fashion and under control of the system's computer to sequentially connect each of its input terminals 166, 168, 170 to the common output terminal 172. Thus, during a first interval, the signal representative of the integrated value of the received energy on a given receiver channel is made to appear on the output line 172 which connects to the input of an analog-to-digital converter 174. In the latter device, the analog signal being held in the circuit 162 is converted to a digital number representative of the received signal. The system's microprocessor 176 periodically samples the output from the analog-to-digital converter and enters the numbers from the various channels into separate memory registers (not shown) within the microprocessor itself. After the computer 176 has stored the multiple receiver input values, it undertakes to perform a data processing function to identify two typical types of flaws commonly found in used tire casings, namely, separations and holes. The first process that the computer performs is to discriminate against signals introduced by tire tread patterns. By using a so-called sliding average filter algorithm whose averaging time corrresponds to, approximately, the time of periodicity of a tread pattern the signal components due to repetitious factors are eliminated. Specifically, if I(k) is defined as a receiver input on the $k^{th}$ computer cycle, the sliding average filter, which is a form of a finite sampled data filter, yields a signal, A(k), where:

$$A(k) = \frac{1}{N} \sum_{i=0}^{N-1} I(k - i)$$

N=8 for most tire tread patterns. Adaptive adjustment of N has been found, experimentally, to be unncessary.

Once the effects of tread patterns are removed for, the computer does a subsequent computation to establish a "baseline" so that predetermined deviations from the baseline can be interpreted as either a hole or a separation type flaw. The baseline computation employs the filtered signal from the tread averaging algorithm as its input and, based upon the following recursion formula, the computer provides additional filtering over a sufficiently long period of time to establish a reasonable baseline. The output from the recursive filter may be defined as B(k) where:

$$B(k) = \left(1 - \frac{1}{M}\right) B(k - 1) + \frac{1}{M} A(k)$$

where M=64 and B(1)=0.01

Having established this baseline, it is compared with the signal from the output of the tread averager to define separations and holes. When a predetermined deviation of the average signal from the baseline is observed by the computer in a first direction (towards zero) it is automatically classified as a separation in that the amplitude of the received energy decreases in traversing a separation. However, if a hole is present, the deviation will extend from the baseline to a larger value in that the amplitude of the received energy increases in passing through the hole rather than through the casing material. If the deviation exceeds a predetermined threshold level it is interpreted as a hole. The system further permits detection of massive separations, i.e., separations that occur over large distances along the periphery of the tire. Specifically, the output of the tread averaging filter is observed by the computer and when it is determined that this output remains in a predetermined level for a specified time period, a massive separation is detected. Stated symbolically if $A(k) > C_H B(R)$ a hole has been detected. If $A(k) < C_S B(k)$ a separation has been detected and if $B(k) < C_M$, a massive separation is indicated, $C_H$, $C_S$ and $C_M$ being predetermined constants. Indications of holes and/or separations are displayed on a display device, 178.

As is indicated in FIG. 10, the microprocessor or computer 176 has a first output line 180 which connects to the astable multivibrator 128 of the transmitter of FIG. 8 for controlling the on and off gating thereof. Furthermore, the computer provides a control signal by way of an output line 182 to the integrate and hold networks for all of the channels simultaneously and thereby determines the time at which the integration is to take place during each cycle. The output on line 184 from the microprocessor 176 carries the requisite control signals for causing the multiplexer 164 to step through its cycle and sequentially connect its input lines 166, 168, etc., to the output line 172. The signals appearing on the output line 186 of the microprocessor are applied to the A/D converter 174 for controlling the time in the cycle that conversion is to take place.

As mentioned, the output of the microprocessor 176 drives a display device 178 which includes a plurality of lights that are selectively illuminated to display the fact that a hole or a separation has occurred, as well as the particular channel on which the defect has been determined to be present. This latter feature permits the operator to more readily determine the precise location on the tire where the defect is located.

Using the ultrasonic inspection device of the present invention, it has been possible to detect flaws that have hitherto been invisible to a human operator, particularly in situations where the tire casings being inspected have high treads or where belt edge separations occur internally in radial tires. While holes generally have been detectable visually, because of workload and operator fatigue, a fair percentage of such holes are missed using visual inspection, resulting in costly returns to get these holes patched. The machine of the present invention easily identifies holes in that there is a marked increase in the amount of energy transmitted through the tire proximate such a hole. Similarly, the presence of an internal void (separation) results in a marked decrease in the energy transmitted through the tire. The system, especially the computing portion thereof, is able to determine the extent of deviation of the received signals from a given baseline and thereby aids the inspector in detecting flaws that have not been detectable, thus reducing the number of faulty casings that must later be scrapped after having undergone costly retreading.

Because circuits for implementing the preamplifier 156, the bandpass filter 158, the demodulator 160 and the sample and hold circuit 162 are all well known and commercially available devices, it is deemed unnecessary to specifically describe such devices in that those of ordinary skill in the art will be able to discern from the teaching herein how to make and use the present invention.

The microprocessor 176 is preferably an INTEL 8085 device. However, other microprocessor systems would be usable. Those skilled in the art will be able to program such a multi processor to cause it to issue pulse type control signals to the transmitter, the receivers' integrate and hold circuits and its multiplexer at predetermined desired times. Further, those persons of ordinary skill in the art will be able to write the detailed computer instructions for carrying out the computations indicated by the formulae set out on pages 18 and 19 hereof. Hence, it is deemed unnecessary to specifically set out herein the machine code for such instruction sequences.

A multiplexer circuit suitable for use as the device 164 as well as A/D converter circuits are commercially available in integrated circuit chips from a number of sources and those desiring additional information on the construction and operation of such devices are referred to the data handbooks of the various integrated circuit manufacturers supplying these devices.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices and that various modifications, both as to equipment details and operating procedures can be affected without departing from the scope of the invention itself.

What is claimed is:

1. In an ultrasonic vehicle tire test system:
   (a) a fixture for holding a tire casing totally in air and rotating same about a central axis, said fixture including an articulated arm which is movable between a first and a second disposition with respect to said tire casing;
   (b) a first transducer array including a plurality of ultrasonic transducers, each producing a directional beam of ultrasonic energy when pulsed by electrical impulses of a predetermined frequency, said first transducer array being affixed to said arm with the individual transducers disposed in a compact cluster arrangement; and
   (c) actuator means connected to said arm for moving said first transducer away from a first disposition outside of the opening defined by a sidewall of said tire casing to a second disposition within said tire casing between the sidewalls with the individual transducers of said first transducer array being in a close but non-contact relationship with respect to the tread portion of said tire casing and oriented to direct their individual beams of ultrasonic energy in a combined fashion so as to span the entire width of said tire casing.

2. Apparatus as in claim 1 wherein said first transducer array comprises:
   (a) a housing having a face plate with at least three ultrasonic transducers mounted thereon at locations corresponding to the vertices of an isosceles triangle, one of said transducers being pointed to project a sound energy wave normal to said face plate and the other of said transducers being pointed to project a sound energy wave at divergent angles from said face plate;
   (b) a generally "T"-shaped sound energy absorbing baffle affixed to said face plate and extending outwardly therefrom with the cross portion of said T-shaped baffle extending between said one of said transducers and said other of said transducers and the vertical portion of said T-shaped baffle extending between said other of said transducers; and
   (c) a roller member journaled to said housing for abutting the inside surface of said tire casing and maintaining said three transducers in a spaced relationship with respect to said inside surface of said tire casing as said casing is rotated.

3. Apparatus as in claim 1 and further including a second transducer array affixed to said fixture and positioned exterior to said tire casing and comprising:
   (a) a generally rectangular box-like housing having a face plate with a plurality of apertures formed therein, each of said apertures containing an ultrasonic transducer having its axis normal to said face plate;
   (b) first and second horizontally extending, parallel roller members journaled to said housing and adapted to abut the outside tread area of a tire casing for maintaining said plurality of transducers in a spaced apart relationship with respect to said tread area of said tire casing as said casing is rotated;
   (c) a pair of vertically extending planar baffle members affixed to the opposed side edges of said box-like housing; and
   (d) means for attaching said housing to said fixture for resiliently urging said rollers against the tread area of said tire casing.

4. Apparatus as in claim 1 wherein said first transducer array comprises:
 (a) a housing including a planar face plate, said face plate having a plurality of vertically aligned apertures;
 (b) means for mounting an ultrasonic transducer in each of said apertures with the axis of said transducers being at different predetermined angles with respect to the plane of said face plate.

5. Apparatus as in claim 1 wherein said articulated arm comprises:
 (a) a first pair of elongated linkages of substantially equal length having one end of each pivotally connected to said fixture;
 (b) a connector member pivotally attached to said first pair of linkages proximate the other ends thereof so as to define a first parallelogram;
 (c) a second pair of elongated linkages of substantially equal length pivotally coupled at one end to said connector member;
 (d) an actuator coupling member pivotally joined to the other ends of said second pair of linkages so as to define a second parallelogram;
 (e) a piston and cylinder having a first end of one of said piston or cylinder pivotally coupled to said fixture at a point displaced a predetermined distance from the pivotal connections of said first pair of linkages to said fixture and a second end of said piston or cylinder connected to said connector member; and
 (f) means affixing said first transducer array to said connector member, the arrangement being such that the withdrawing of said piston into said cylinder results in a movement of said first transducer array in a direction generally parallel with an edge of said fixture, followed by a movement of said first transducer array generally perpendicular to said edge of said fixture for a second predetermined distance.

6. Apparatus as in claim 5 and further including a stop member disposed in the path of rotation of said cylinder for arresting the rotation thereof at a predetermined orientation.

7. Apparatus as in claim 5 and further including a tension spring connected bewteen said cylinder and said fixture.

* * * * *